US005578769A

United States Patent [19]
Warrington et al.

[11] Patent Number: 5,578,769
[45] Date of Patent: Nov. 26, 1996

[54] METHODS AND APPARATUS FOR UNDISTURBED SUBSURFACE SOIL CHEMISTRY SAMPLING

[76] Inventors: Gordon E. Warrington, 8125 Turman Ct., Fort Collins, Colo. 80525; Earl O. Skogley, 3535 Stucky Rd., Bozeman, Mont. 59715

[21] Appl. No.: 171,563

[22] Filed: Dec. 20, 1993

(Under 37 CFR 1.47)

[51] Int. Cl.⁶ .................................................. G01N 1/22
[52] U.S. Cl. .................................................. 73/864.74
[58] Field of Search .................... 73/863.21, 863.23, 73/863.25, 863.31, 864.31, 864.43, 864.73, 864.74

[56] References Cited

U.S. PATENT DOCUMENTS

| | | |
|---|---|---|
| 2,793,527 | 5/1957 | Turner, Jr. et al. . |
| 3,374,678 | 3/1968 | McGuckin .................... 73/864.74 |
| 3,774,718 | 11/1973 | Igarashi et al. . |
| 3,962,915 | 6/1976 | Jezequel . |
| 4,445,788 | 6/1984 | Twersky et al. . |
| 4,530,236 | 7/1985 | Van den Berg . |
| 4,543,820 | 10/1985 | Handy et al. . |
| 4,726,239 | 2/1988 | Boggess et al. . |
| 4,993,874 | 2/1991 | Klusman . |
| 5,009,112 | 4/1991 | Lawrence et al. .................... 73/863.52 |
| 5,101,917 | 4/1992 | Abdul et al. . |
| 5,235,863 | 8/1993 | Bailey et al. .................... 73/863.21 |

OTHER PUBLICATIONS

Nitrate Movement Under Corn and Fallow Conditions, Long, F. L., and M. G. Huck, Soil Science of America Journal, Jul.–Aug. 1980, vol. 44, #4.

Minirhizotrons: A Summary of Methods and Instruments in Current Use, Brown, D. A., and D. R. Upchurch, American Society of Agronomy, 1987, Crop Science of Americal and Soil Science Society of America, 677 S. Segoe Rd., Madison, WI 53711 USA, Minirhizotron Observation Tubes: Methods and Applications for Measuring Rhizosphere Dynamics, ASA Special Publication No. 50.

Applications and Limitations of Rhizotrons and Minirhizotrons, McMichael, B. L. and H. M. Taylor, American Society of Agronomy, 1987, Crop Science Society of America, and Soil Science Society of America, 677 S. Segoe Rd., Madison, WI 53711 USA, Minirhizotron Observation Tubes: Methods and Applications for Measuring Rhizosphere Dynamics, ASA Special Publication No. 50.

The Universal Bioavailability Environment/Soil Test Unibest, Skogley, Earl O., 23 Commun. Soil Sci. Plant Ana. 2225, published Dec. 23, 1992.

*Primary Examiner*—Robert Raevis
*Attorney, Agent, or Firm*—Luke Santangelo

[57] ABSTRACT

A subsurface sampling system which is designed to avoid disturbance of the sample point allows for repetitive insertion of a sampling means, such as a resin capsule, to allow repetitive sampling at a given location. Through variation in the design natural percolation and angled positioning may be accommodated. A shield and other means for diverting external substances such as ground water, rain, and the like are incorporated as well as a cap which integrates with a spring or other type of tension means to appropriately position the sampling means adjacent to the particular point desired to be sampled. A central access chamber and a variety of sampling passageways are provided for in applications in which repetitive sampling at multiple sites is desired.

42 Claims, 2 Drawing Sheets

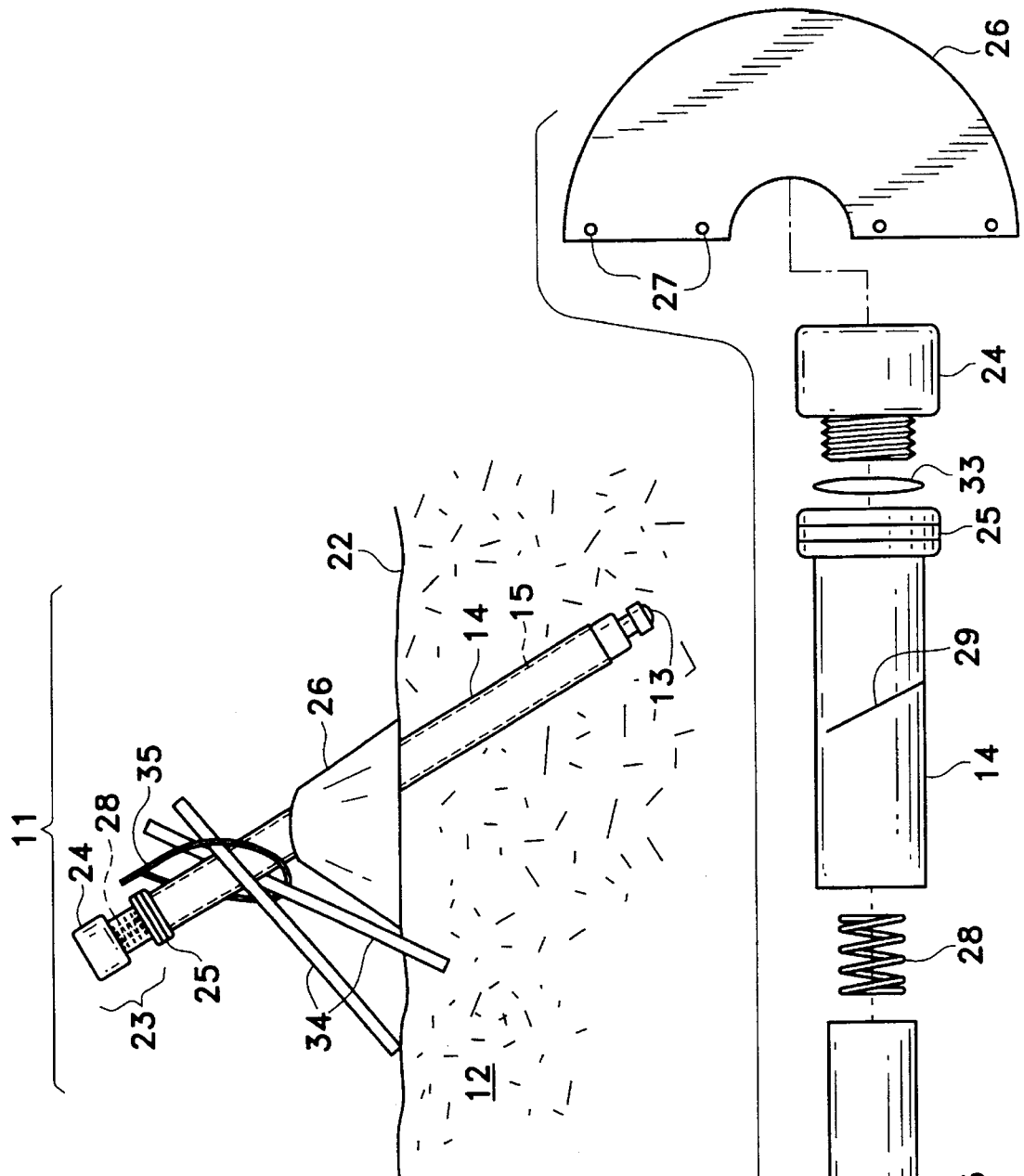

METHODS AND APPARATUS FOR UNDISTURBED SUBSURFACE SOIL CHEMISTRY SAMPLING

BACKGROUND OF THE INVENTION

The present invention relates generally to techniques for sampling subsurface substances. Specifically, the invention focuses both methods and apparatus for soil chemistry sampling which do not substantially disturb the environment to be sampled.

The concept of chemically sampling a subsurface substance such as soil, biological products (fungi, bacteria, flora, etc.), water content, or other substances has been known for many years. Through the general technique, a subsurface location is accessed and then sampled in order to ascertain its chemical characteristics. These characteristics can include a great variety of attributes including but not limited to the substance chemical makeup, its moisture content, and the like.

One of the challenges which those skilled in the art have faced is the fact that the sampling action itself can impact both the immediate test results as well as the subsurface character. Not only has this resulted in the sampling action itself being closely scrutinized, but it has also caused those skilled in the art to often question results achieved. This is especially true when attempting repetitive sampling for chemical composition at the same point. In such applications, the technique, prior to the present invention, has often been to physically retrieve a small portion of the subsurface substance and to then analyze that retrieved material.

Naturally, in any retrieval of a substance, that substance is disturbed. In spite of this almost obvious aspect, some have characterized such test methodology as a methodology which does not disturb the subsurface substance. This characterization alone may have served to lead those skilled in the art away from the direction taken by the present invention. The present invention significantly overcomes the limitations that those skilled in the art have faced as a result of such techniques; it achieve substantially undisturbed testing of subsurface chemistry.

Perhaps surprisingly, the present invention discloses both methods and apparatus which overcome these limitations through very simple means. This may in part be due to the fact that while those skilled in the art had recognized a long-felt need for the results which the present invention achieves, they had not fully appreciated the nature of the problem. In fact, to some degree those skilled in the art may have even taught away from the direction taken by the present invention. By focusing upon testing or sampling at different locations rather than at different times at the same location they may have also been directed away from the present invention. Although those skilled in the art have in other aspects improved sample acquisition systems, to a large part their efforts have been directed more towards sample systems which retrieve small portions of the substance rather then sample systems which did not substantially disturb the substance. For instance U.S. Pat. No. 5,101,917 to Abdul represents an improvement in a soil retrieval assembly. Unlike the present invention it clearly disturbs the soil it is retrieving. Other art has been directed to other fields, such as root growth and the like; these are not applicable as they do not deal with the unique problems of chemistry sampling where actual contact can be necessary but where even small impacts from such contact can have significant effects on the present and future state of the point sampled.

To some degree, those skilled in the art may even have failed to recognize that by achieving substantially undisturbed sampling, time dependent sampling could replace sampling at different locations within a particular subsurface. To the extent those skilled in the art directed their efforts to more complex sampling systems, they also may have failed to realize the efficiencies with which a simple device could achieve repetitive sampling. Thus, the simplicity with which the present invention achieves solutions to the problems which had existed may have also contributed to leading those skilled in the art away from the direction taken.

SUMMARY OF THE INVENTION

The present invention involves both methods and apparatus which achieve substantially undisturbed subsurface substance sampling. In one embodiment the invention may involve a device which incorporates a casing placed at an angle into a soil or other surface. Into this casing is inserted an arm which acts to position a sample means at some preselected subsurface point. This sample means may be held gently against the point to be tested and through the use of some absorbent material can actually sample the substance without substantially disturbing it. In order to assure accuracy and to accommodate the needs of repetitive testing, the surface access point can be shielded and remotely located from the actual point tested. This access may also be covered to avoid the introduction of external substances both in between tests and while acquiring data on the point to be sampled Accordingly, it is a goal of the invention to achieve sampling without substantially disturbing the point to be sampled. In keeping with this goal the invention allows accurate, repetitive sampling and minimizes (or even completely avoids), impacts on the test environment from the sampling action. Thus the invention retains the site as natural as possible for later unimpacted sampling.

Another goal of the present invention is to accommodate existing as well as developing sampling technologies. In accordance with this goal, the techniques and devices disclosed are very general in nature so that they might be adapted to accommodate future sampling technologies. As one type of sampling technology the present invention incorporates absorbent sampling systems such as resin capsule sampling. The invention also is designed to accommodate both insitu or remote analysis capabilities.

Yet another goal of the present invention is to provide an inexpensive reusable system. Although in accommodating one sampling technology, the system does accommodate the possibility of utilizing disposable sampling technology, the main portions of the sampling system are generally reusable.

A further goal of the present invention is to provide for a sampling system which does not require a high degree of skill in order to implement. Thus many facets of methods and the apparatus are designed to be easily utilized.

Yet one more goal of the invention is to allow for both multiple site or multiple depth sampling through one placement. Again, this has been designed to be easily implemented without difficulty.

Naturally further objects of the invention are disclosed throughout other areas of the specifications and claims.

BRIEF DESCRIPTION OF DRAWINGS

FIG. 1 is a side view of one type of single-site repetitive sampling system according to the present invention.

FIG. 2 is an exploded view of an embodiment similar to that shown in FIG. 1.

DETAILED DESCRIPTION OF THE PREFERRED EMBODIMENTS

Figure 3:
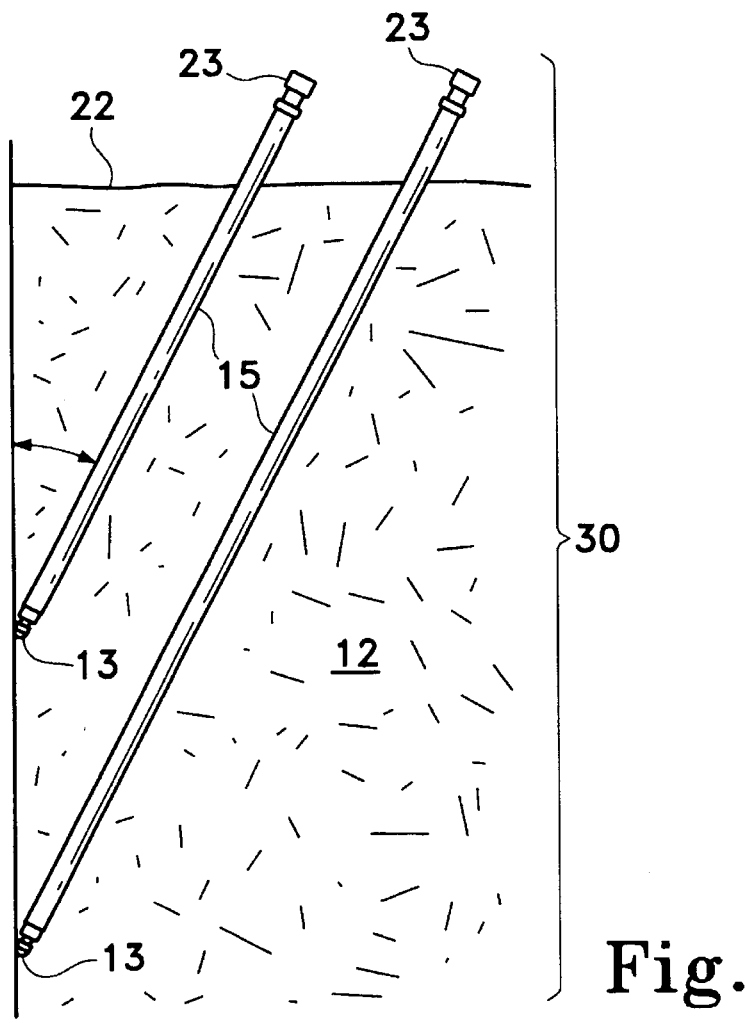
FIG. 3 is a cross section view of one multiple-site casing as it might appear when installed.

As can be seen from the drawings, the basic concepts of the present invention may be embodied in different ways. FIG. 1 shows a side view of a single-site repetitive sampling system. The sampling system (11) is shown as placed in an angled manner within a subsurface (12). Through a prior determination, sampling system (11) is positioned so as to access a specific point (13) which is established as a point at which it is desirable to ascertain the substance's chemistry. Importantly it should be understood that due to the nature of soils and other subsurface substances, the actual substance encountered at point (13) can vary based upon location. Thus it is desirable to not only avoid disturbing the subsurface substance at point (13), it is also desirable to be able to accurately sample at the same point each time. In order to accomplish this, sampling system (11) may incorporate casing (14). Casing (14) may be designed to be either fixed or removable. Importantly, casing (14) may be selected so as to allow the placement within it of some sampling means. As those skilled in the art would readily understand, the sampling means may include a variety of technologies.

The step of establishing the point to be sampled may include not only the location at which to sample, but also the depth desired to be sampled. This depth may be in the vadose zone, that is to the water table. It may also be below the permanent water table. By utilizing different length designs, naturally different depth may be sampled. Further, as shown in FIG. 3, by utilizing a number of different lengths and stacking several sampling systems, a vertical cross section can be constructed. This also illustrates how placing the various sampling systems in an angled configuration as shown in FIGS. 1 and 3 serves as a means for avoiding substantial disturbance as well. In the stacked configuratiuon shown in FIG. 3, the locations at surface level (22) may also be established on a contour line so that true depths are not influenced by the particular terrain.

Referring to FIG. 2, the details of the sampling means are further shown. As mentioned earlier the sampling means may be designed so as to fit within casing (14). As shown, this may include the utilization of arm (15). As shown, both casing (14) and arm (15) may be cylindrical pieces of tubing in which the outer diameter of arm (15) is less than the inner diameter of casing (14). Thus, arm (15) may be designed to fit roughly coaxially within casing (14). Importantly, arm (15) serves to position some sampling means at point (13). This sampling means may be located at the end of arm (15) as shown.

As shown in FIG. 2 the sampling means may be some type of absorbent substance. Referring to FIG. 2 it can be seen that the absorbent sampling means (16) may consist of some type of encapsulated absorbent, such as a resin, which is contained within a porous encapsulation (17). This porous encapsulation (17) may consist of a fine mesh screen or some other substance. As shown in the particular embodiment drawn in FIGS. 1 and 2, the porous encapsulation (17) may serve as a sampling boundary which, when in place, touches the subsurface substance at point (13) so that it is adjacent to point (13). Further, in one embodiment porous encapsulation (17) may be shaped as a spherical screen. This spherical screen may integrally or separately involve a hemispherical boundary (18). Hemispherical boundary (18) can serve to assist in mounting absorbent sampling means (16) to arm (15).

As shown, the mounting of the absorbent sampling means may be through the use of retainer means (19). Retainer means (19) may be designed with some type of hole (20) through which absorbent sampling means (16) may be exposed to point (13) and yet still be responsive to retaining means (19). Retainer means (19) may threadably engage arm (15) through the use of arm threads (21) as shown on arm (15). Through this type of technique, retainer means (19) can be easily removed to allow retrieval of absorbent sampling means (16) for replacement or analysis. Again, by properly sizing retainer means (19) the entire sampling means, that is, arm (15) absorbent sampling means (16), and retainer means (19) can be positioned through casing (14). This allows access from one end of casing (14) when casing (14) is placed as shown in FIG. 1.

Referring back to FIG. 1, several other attributes can be understood. First, it can be seen that sampling system (11) may extend above surface level (22). Although this is not necessary this may be achieved in instances such as when it is desirable to easily locate sampling system (11). In such instances the upper end of sampling system (11) may even be brightly colored or otherwise marked. Regardless whether the upper end of sampling system (11) is placed above or below surface level (22), it may be designed so as to provide an access location (23). Access location (23) can serve to allow complete retrieval of the sampling means. Access location (23) may also be shielded or covered as shown. This can be important. Since one of the goals of the present invention is to avoid impacting the site to be sampled through the sampling actions themselves, it is desirable to design a system which does not cause the introduction of any external substances. In this regard, it is desirable to avoid rain, ground water, or other surface originating or external substances from having access or some easier passageway to point (13). In order to achieve this the invention can include several aspects.

First, as shown in FIG. 1, access location (23) may be covered through the use of cap (24). Cap (24) may engage casing (14) or some other aspect of sampling system (11) or may merely cover some portion of sampling system (11). As shown, cap (24) is designed to engage casing (14) to prevent the introduction of any external substances at access location (23). In one design cap (24) threadably engages casing (14) through the use of casing threads (25). Casing threads (25) allow easy removal of cap (24) and may also serve to allow positive engagement of cap (24) so as to serve in conjunction with the spring described later. Cap (24) may also be sealed to casing (14) through the inclusion of some type of seal (33). Seal (33) may serve to provide necessary isolation of point (13) from outside elements. As such it may be positioned in between casing (14) and cap (24) or may likewise be positioned in between shield (26) and casing (14).

A second facet of avoiding any introduction of external substances is also shown in FIG. 1 as shield (26). Shield (26) may simply be a semi-circular sheet cut as shown in FIG. 2, a bag, or some other design. As shown, shield (26) may include snaps or other shield retaining means (27) which when engaged may cause the sheet to form a conical surface. In this fashion shield (26) may form a surface responsive to casing (14) which serves to divert external substances away from casing (14). This can be important even if only within the vicinity of access location (23) as passages or spaces can form through the expansion and contraction of the various substances along casing (14) thus allowing external substances originating at the surface to flow easily to point (13). In order to prevent this introduction of substances, shield (26) can be designed to direct such substances away from casing (14) as shown. Further, shield (26) may be designed so as to not cover vertically above point (13). This aspect of shield (26) may be included to allow natural percolation from surface level (22) through to point (13) to allow as natural and unimpacted an environment as possible at point (13).

As shown in FIGS. 1 and 2, sampling system (11) may also incorporate some type of tension means such as spring (28). While naturally a great variety of tension means including but not limited to expandable elastic materials may be incorporated, through the use of some type of tension means such as spring (28) accurate sampling can be assured. This is achieved by allowing spring (28) to be responsive to both cap (24) and arm (15). As shown in FIG. 1 this is achieved when arm (15) is inserted within casing (14). By attaching spring (28) to the end of arm (15), when cap (24) is threaded onto casing (14), its inner surface may push upon spring (28) and thus urge arm (15) against point (13). Through this technique, the sampling means, in this case absorbent sampling means (16) touches point (13) with some predetermined amount of force which may be maintained throughout the sampling process. This force may be determined by ascertaining not only the angle at which casing (14) is placed in the ground but also the nature of the particular subsurface substance anticipated to be encountered. For instance, in horizontal sampling situations, the tension means may provide a greater degree of force than in vertical situations. Further, in instances in which the particular subsurface substance encountered is very fragile, the tension means may provide a lesser degree of force. In this fashion the amount of force and thus the amount of disturbance avoided can be controlled. In applications utilizing the preferred angular placement of sixty degree angles from the horizontal (as shown in FIGS. 1 & 3), at typical depths it has been found that a spring with a force of about 1.5 pounds per inch compression works well. Thus spring (28) can substantially establish a prespecified force.

Finally with respect to FIGS. 1 and 2, it can be seen most clearly in FIG. 2 that casing (14) may include some type of depth indicator (29). Depth indicator (29) may be a single straight or angled line positioned on casing (14). This indicator may provide the person placing it or utilizing sampling system (11) with an immediate and accurate determination of the particular depth involved at the specified angle. Further, depth indicator (29) may actually include a series of lines or other types of indication to allow for multiple depth placement. Naturally, depth indicator (29) may also be included on arm (15) or on other aspects of sampling system (11) as appropriate.

Figure 4:
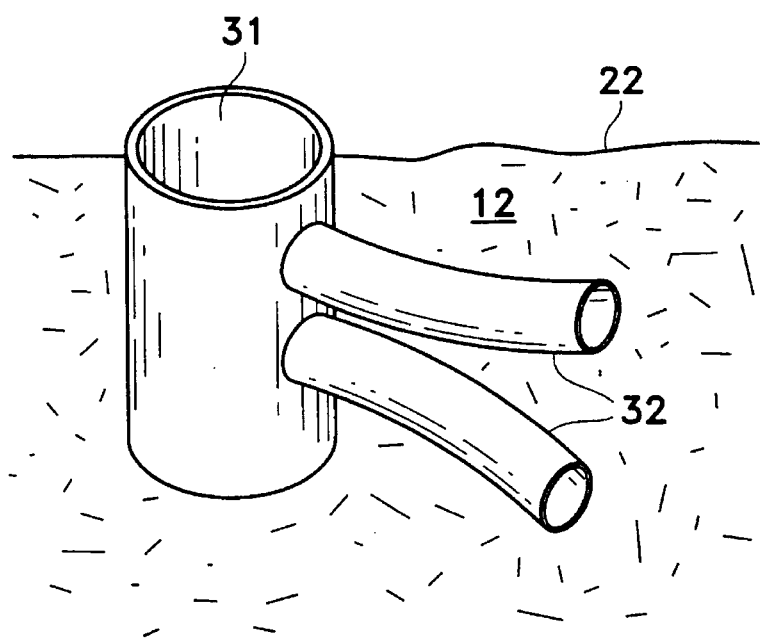
FIG. 4 is a cross section view of stacked, multiple placements as may be used in obtaining a vertical cross section.

Referring to FIG. 4, one type of multiple-site sampling system (30) can be readily understood. Multiple-site sampling system (30) may consist of one or more main access chambers (31). Connected to main access chamber (31) may consist a number of sampling passageways (32). Similar to the single-site sampling system (11) shown in FIG. 1, each sampling passageway (32) may act similar to casing (14) to allow some sampling means to be placed within sampling passageways (32) for multiple-site sampling. As shown, in FIG. 4, sampling passageways (32) may be curved and may thus allow the use of some type of flexible arm as a sampling means. Further, the aspects disclosed with respect to multiple-site sampling system (30) may be adapted for even single-site sampling. Thus, casing (14) may be curved; may provide a vertical access location and may yet allow unimpeded percolating through to point (13). Further, only main access chamber (31) may allow access. It may also be placed beneath surface level (22). Additionally, the tension means may be incorporated in some other fashion such as through capping sampling passageways (32) or otherwise engaging either main access chamber (31), sampling passageway (32), or some other structure or surface. By providing more than one sampling passageway (32), each sampling passageway (32) may have a unique depth at which it achieves sampling. Thus, repetitive sampling can be achieved at a variety of depths even at locations where one point is directly above another. In this fashion sampling can also be achieved without substantially disturbing the sampling above and below that particular spot.

Again, an important aspect of sampling system (11) is that it may include some type of means for avoiding any substantial disturbance of the subsurface substance. Since there are a great variety of ways to achieve this, the means for avoiding is intended to encompass all of these techniques. The particular structure should not limit it as it may include tension control when appropriately configured, the tension means or spring discussed earlier (again, when appropriate configured), the angling of arm (15) or a casing (14) such as shown through which a sampling means may be inserted, or even the absorbent substance boundary such as porous encapsulation (17). No doubt a great variety of other types of controls may be incorporated. As such each is intended to fall within the scope of a means for avoiding as defined in the present invention. All that is necessary is that some type of element act to avoid any substantial disturbance of the subsurface substance. By "substantial" it is intended that the amount of disturbance be designed to accommodate the particular type of sampling technique utilized and the substances encountered. In most applications since most accurate testing will occur with a minimal amount of disturbance, it is intended that, for such applications, substantial disturbance be this relatively small amount. Certainly, any removal of substance would not fall within the concept of avoiding substantial disturbance. The means for avoiding any substantial disturbance may act with respect to point (13) or above point (13).

Having discussed generally the broad variety of devices which might be utilized in the present invention, the methods for achieving its goals can be easily understood. To some extent these methods are also described in the article by Earl O. Skogley entitled *"The Universal Bioavailability Environmental/Soil Test Unibest"*, Commun. Soil Sci Plant Anal , 23 (17–20), 2225–2246 (1992). This article is hereby incorporated by reference in to this patent. Specifically, the method may incorporate several steps. Initially a particular location and depth for a particular point below the surface level is established. A sample means is then positioned adjacent to that point. This may typically be achieved by drilling or auguring or otherwise establishing some type of passage to allow the sample means to be positioned adjacent to the particular point desired to be sampled. Importantly, prior systems in which some type of probe was merely driven into the ground may not be appropriate in most applications. This is because the act of driving in a probe may greatly disturb the subsurface substance desired to be sampled. By drilling disturbance can often be minimized.

In drilling the passageway, it may be desirable to provide for drilling at an angle as shown in FIGS. 1 & 3. In this fashion the particular point to be accessed is not accessed from directly above. This is important because it may be desirable to allow natural percolation to occur from surface level (23) through to point (13). Since natural percolation and the like are integral processes to the establishment of the particular subsurface substance chemistry desired to be sampled, any interruption of or change in them may impact that chemistry. Such changes may also impact the absorption or diffusion rate for both the substance sampled and the sampling means. Thus, it may be important to not only avoid any substantial disturbance of the subsurface substance at the point to be sampled but also to avoid such disturbances above that point. It can also be important to avoid covering the surface as rain and other surface impacts can potentially impact the subsurface substance's chemistry. The facet of allowing natural percolation can be particularly important when utilizing repetitive sampling at the same point. In such instances, substantial disturbances are avoided by the present invention.

When drilling to initially locate casing (14), a variety of techniques can be used. Preferably, the drilling is first accomplished with a larger bit to allow placement of casing (14). Before completing the first drilling, the bit may also be cleaned to avoid any contamination at point (13). In addition dry drilling is preferred to keep point (13) as undisturbed as possible. Once the last 1" or so is drilled with a clean bit, a second bit may be utilized to complete the final drilling at a lesser diameter as appropriate for the sampling means. All of this drilling may be achieved as some angle, such as sixty degrees from the horizontal, to avoid disturbing above point (13) as well as to avoid the artifical introduction of root systems at point (13).

As discussed earlier, when placing the sampling means a passageway may be established. This passageway may either be encased or not. Once established the sampling means may be inserted so that the end of the sampling means just touches point (13) from which data is desired. The degree to which the sampling means touches point (13) may naturally vary depending upon both the sampling means and the nature of the particular subsurface substance to be sampled, however, it can be important that the amount of touching not be sO strong as to cause any substantial disturbance at point (13). As mentioned earlier the amount of force can be controlled through some type of tension means. This tension means can establish a prespecified force—that is a force which has been determined to be the appropriate amount of force given the particular subsurface substances and the particular sampling means employed. Once established, the tension means may also act to maintain that particular force during the sampling step. This can be important as certain types of sampling means may require larger amounts of time in order to acquire their data. As one aspect of the invention, the sampling means may be kept in contact with the subsurface substance for a suitable time. This may vary from seconds to even as many as four days or more depending upon the particular sampling means employed or events desired to be sampled. For instance, when using an absorbent sampling means (16) several days may be required in order to sufficiently acquire data with regard to the subsurface substance's chemistry. In addition, long term sampling (ie. weeks or even months) may be necessary when the effects of transient events such as storms and the like are desired to be sampled.

Once the sampling means has accumulated its data, the sampling means may be retrieved for separate analysis leaving casing (14) intact for a later test. While in the preferred embodiment shown in FIG. 1, the sampling means is an absorbent sampling means (16), by retrieving the sampling means all that is actually necessary is that the actual data be retrieved. Thus, particular sampling means which merely provide electronic output or other types of data could fall within the concept of retrieving the sampling means because the data itself is retrieved. In the present invention absorbent sampling means (16) would be physically retrieved. Thus, sampling system (11) need not include analysis or other expensive equipment. Rather, in this one embodiment absorbent sampling means (16) (as well as some other type of similar sampling means) would merely be retrieved and transported to a laboratory or other location for actual analysis. This analysis might take a great variety of forms as those skilled in the art would readily understand. Finally, the result of the analysis would be that the chemistry of the subsurface substance would ultimately be ascertained. Again, this may be particularized for specific chemistries or may be general.

To assure unimpacted sampling, one technique disclosed by the present invention is to continuously avoid any substantial disturbance of the area during a variety of steps. This may occur during positioning, during sampling, or even during retrieval. The avoidance of substantial disturbance may take place not only at the point to be sampled but also above the point and even at the surface level. Since percolation tends to occur in almost a vertical realm, it may be possible to avoid disturbance in a narrow cylinder or cone above point (13). Naturally, for particular substances the extent of disturbance and even the size of the cone involved may vary.

Naturally, with respect to the sampling means, as those skilled in the art would readily understand the particular sampling means can be not only varied but can be configured to test for specific chemical compositions. Thus, when only a particular substance is of interest the entire technique can be optimized through configuring the sampling means appropriately. By using absorbent sampling means (16), the bioavailability can be ascertained as those skilled in the art would readily understand. Absorbent sampling means (16) also can be a relatively low cost type of sampling means. Further, when repetitive sampling is desired, the sampling means can be retrieved, replaced, and reinserted. This may involve removing only the sampling means and leaving some type of casing intact in order to more efficiently accommodate later testing.

Finally, the entire sampling system (11) may incorporate some type of support system. This support system may simply be rods (34) attached through a strap (35). This would allow the sampling system to avoid any shifting or moving over time and may be especially helpful in instances in which particularly shallow sampling is desired. In these instances it may be helpful to support casing (14) by a support. Generally it is believed that the support system is not necessary unless sampling is achieved at depths of less than 10 inches. Naturally, thismay vary due to the particular nature of the subsurface substance or even the particular designs of sampling system (11). Such a support system might take a great variety of forms and might be of non-contaminating material (as well as other components of the entire system) as those skilled in the art would readily recognize.

The foregoing discussion and the claims which follow describe the preferred embodiments of the present invention. Particularly with respect to the claims, it should be understood that changes may be made without departing from its essence. In this regard, it is intended that such changes would still fall within the scope of the present invention. It simply is not practical to describe and claim all possible revisions to the present invention which may be accomplished. To the extent such revisions utilize the essence of the present invention, each would naturally fall within the breadth of protection encompassed by this patent. This is particularly true for the present invention since its basic concepts and understandings are fundamental in nature and can be broadly applied.

We claim:

1. An method for sampling the chemistry of a subsurface substance comprising the steps of:
   a. establishing a point beneath a surface level at which it is desirable to ascertain a substance's chemistry;
   b. positioning a sample means adjacent to said point wherein said point is situated on a vertical line beneath said surface level and wherein said step of positioning a sample means adjacent to said point comprises the step of angled drilling with respect to said vertical line; and
   c. avoiding any substantial disturbance of the subsurface substance at said point; and then
   d. sampling said substance's chemistry through action of said sample means while continuing said step of avoiding any substantial disturbance at said point; then
   e. retrieving said sample means;
   f. analyzing said sample means;
   g. ascertaining the chemistry of the subsurface substance at said point;
   h. avoiding any substantial disturbance of a subsurface substance above said point; and
   i. repetitively sampling said substance's chemistry. at said point wherein said step of avoiding any substantial disturbance of a subsurface substance above said point and said step of avoiding any substantial disturbance of the subsurface substance at said point are each simultaneously accomplished while accomplishing said step of positioning a sample means adjacent to said point and while accomplishing said step of sampling said substance's chemistry through action of said sample means and while accomplishing said step of retrieving said sample means.

2. An method for sampling the chemistry of a subsurface substance as described in claim 1 and further comprising the step of assuring natural pertelation reaches said point.

3. An method for sampling the chemistry of a subsurface substance as described in claim 1 and further comprising the step of preventing the introduction of external substances at said point.

4. An method for sampling the chemistry of a subsurface substance as described in claim 3 wherein sample point has an access location and wherein said step of preventing the introduction of external substances at said point comprises the step of diverting said external substances away from said access location.

5. An method for sampling the chemistry of a subsurface substance as described in claim 4 wherein said step of diverting said external substances away from said access location further comprises the step of capping said access location.

6. An method for sampling the chemistry of a subsurface substance as described in claim 4 wherein said step of sampling said substance's chemistry further comprises the step of acquiring data from said sample for a suitable time.

7. An method for sampling the chemistry of a subsurface substance as described in claim 1 and further comprising the step of prespecifying the specific chemical aspects to be sampled.

8. An method for sampling the chemistry of a subsurface substance as described in claim 7 and further comprising the step of configuring said sample means as appropriate for said specific chemical aspects.

9. An method for sampling the chemistry of a subsurface substance as described in claim 1 wherein said sample means is an encapsulated absorbent.

10. An method for sampling the chemistry of a subsurface substance as described in claim 1 and further comprising the step of assuring natural percolation reaches said point.

11. An method for sampling the chemistry of a subsurface substance as described in claim 1 or 2 wherein said sample means has an end and wherein said step of positioning a sample means adjacent to said point comprises the steps of:
    a. drilling from a location at said surface level to said point to establish a passageway;
    b. inserting said sample means within said passageway; and
    c. touching the end of said sample means to said point.

12. An method for sampling the chemistry of a subsurface substance as described in claim 11 and further comprising the steps of:
    a. substantially establishing a prespecified force between the end of said sample means and said point; and
    b. maintaining said force while accomplishing the step of sampling said substance's chemistry through action of said sample means.

13. An method for sampling the chemistry of a subsurface substance as described in claim 12 wherein said sample means is an encapsulated absorbent.

14. An method for sampling the chemistry of a subsurface substance as described in claim 10 wherein said step of positioning a sample means adjacent to said point comprises the steps of:
    a. angled drilling from a location at said surface level to said point establish a passageway;
    b. inserting a casing within said passageway;
    c. inserting said sample means within said casing; and
    d. touching the end of said sample means to said point.

15. An method for sampling the chemistry of a subsurface substance as described in claim 14 and further comprising the steps of:
    a. substantially establishing a prespecified force between the end of said sample means and said point; and
    b. maintaining said force while accomplishing the step of sampling said substance's chemistry through action of said sample means.

16. An method for sampling the chemistry of a subsurface substance as described in claim 15 wherein said sample means is an encapsulated absorbent.

17. An method for sampling the chemistry of a subsurface substance as described in claim 14 or 15 wherein said step of retrieving said sample means comprises the step of removing said sample means while leaving said casing intact.

18. An method for sampling the chemistry of a subsurface substance as described in claim 17 and further comprising the step of preventing the introduction of external substances at said point.

19. An method for sampling the chemistry of a subsurface substance as described in claim 18 wherein sample point has an access location and wherein said step of preventing the introduction of external substances at said point comprises the step of diverting said external substances away from said access location.

20. An method for sampling the chemistry of a subsurface substance as described in claim 19 wherein said step of diverting said external substances away from said access location further comprises the step of capping said access location.

21. An method for sampling the chemistry of a subsurface substance as described in claim 19 wherein said step of sampling said substance's chemistry further comprises the step of acquiring data from said sample for a suitable time.

22. An method for sampling the chemistry of a subsurface substance as described in claim 1 wherein said step of positioning a sample means adjacent to said point comprises the steps of:
   a. drilling from a location at said surface level to said point establish a passageway;
   b. inserting a casing within said passageway;
   c. inserting said sample means within said casing; and
   d. touching the end of said sample means to said point.

23. A device for sampling a subsurface substance at a point comprising:
   a. a sample means;
   b. an arm capable of positioning said sample means at a point beneath a surface level at which it is deskable to ascertain a substance's chemistry wherein said point is situated on a vertical line beneath said surface level and wherein said arm is angled with respect to said vertical line;
   c. a means for avoiding any substantial disturbance of the subsurface substance;
   d. casing wherein said arm is capable of being positioned within said casing;
   e. a cap engagable withsaid casing; and
   f. a shield capable of being positioned responsive to said casing wherein said shield is removable and comprises a flexible semicircular sheet.

24. A device for sampling a subsurface substance at a point as described in claim 23 wherein said casing comprises:
   a. a main access chamber; and
   b. at least two sampling passageways.

25. A device for sampling a subsurface substance at a point as described in claim 24 wherein said sampling passageways are at more than one depth below said surface level.

26. A device for sampling a subsurface substance at a point as described in claim 25 wherein said arm is flexible.

27. A device for sampling a subsurface substance at a point as described in claim 23 wherein said arm is capable of being positioned coaxially within said casing.

28. A device for sampling a subsurface substance at a point as described in claim 27 wherein said sample means comprises:
   a. an absorbent; and
   b. a porous encapsulation.

29. A device for sampling a subsurface substance at a point as described in claim 28 wherein said sample means is removable.

30. A device for sampling a subsurface substance at a point as described in claim 29 and further comprising a retainer means wherein said retainer means is capable of attaching said sample means to said arm.

31. A device for sampling a subsurface substance at a point as described in claim 30 wherein said retainer means threadably engages said arm.

32. A device for sampling a subsurface substance at a point as described in claim 31 wherein said porous encapsulation comprises a spherical screen having a hemispherical boundary and wherein said hemispherical boundary is responsive to said retainer means.

33. A device for sampling a subsurface substance at a point as described in claim 27 and further comprising a depth indicator attached to said casing.

34. A device for sampling a subsurface substance at a point as described in claim 27 and further comprising a support structure which holds said casing in a fixed position relative to said surface level.

35. A device for sampling a subsurface substance at a point as described in claim 27 wherein said casing has an access location and further comprising a seal in the vicinity of said access location.

36. A device for sampling a subsurface substance at a point as described in claim 35 and further comprising a spring and wherein both said cap and said arm are responsive to said spring.

37. A device for sampling a subsurface substance at a point as described in claim 23 wherein said cap threadably engages said casing.

38. A device for sampling a subsurface substance at a point as described in claim 23 wherein said means for avoiding any substantial disturbance of the subsurface substance comprises:
   a. a sampling boundary which defines the edge of said sample means and is adjacent to said point at which it is desirable to ascertain the substance's chemistry; and
   b. a tension means.

39. A device for sampling a subsurface substance at a point as described in claim 23 wherein said means for avoiding any substantial disturbance of the subsurface substance comprises a tension means.

40. A device for sampling a subsurface substance at a point as described in claim 39 wherein said tension means comprises a spring.

41. A device for sampling a subsurface substance at a point as described in claim 23 wherein said sample means has a sampling boundary and wherein said means for avoiding any substantial disturbance of the subsurface substance comprises said sampling boundary.

42. A device for sampling a subsurface substance at a point as described in claim 23 wherein said arm is angled and wherein said means for avoiding any substantial disturbance of the subsurface substance comprises said angled arm.

* * * * *